(12) United States Patent
Mori et al.

(10) Patent No.: US 7,867,210 B2
(45) Date of Patent: Jan. 11, 2011

(54) ABSORBENT ARTICLE

(75) Inventors: Yosuke Mori, Ehime (JP); Shinichi Kouno, Ehime (JP); Tomoka Kamoto, Ehime (JP)

(73) Assignee: Daio Paper Corporation, Ehime (JP)

( * ) Notice: Subject to any disclaimer, the term of this patent is extended or adjusted under 35 U.S.C. 154(b) by 146 days.

(21) Appl. No.: 11/665,469

(22) PCT Filed: Oct. 14, 2005

(86) PCT No.: PCT/JP2005/019361

§ 371 (c)(1),
(2), (4) Date: Aug. 24, 2007

(87) PCT Pub. No.: WO2006/041227

PCT Pub. Date: Apr. 20, 2006

(65) Prior Publication Data

US 2008/0108966 A1 May 8, 2008

(30) Foreign Application Priority Data

Oct. 14, 2004 (JP) .............................. 2004-300459
Mar. 3, 2005 (JP) .............................. 2005-059461

(51) Int. Cl.
*A61F 13/15* (2006.01)
(52) U.S. Cl. .................. 604/385.19; 604/302; 604/324; 604/358; 604/365; 604/381; 604/378; 604/366; 156/164; 156/566; 156/301; 156/292; 156/291; 156/298; 156/299; 156/300
(58) Field of Classification Search ............... 604/378, 604/366, 385
See application file for complete search history.

(56) References Cited

U.S. PATENT DOCUMENTS

| | | | | |
|---|---|---|---|---|
| 2,837,095 A | * | 6/1958 | Stevenson | 604/354 |
| 6,168,584 B1 | * | 1/2001 | Allen et al. | 604/385.19 |
| 6,248,098 B1 | * | 6/2001 | Sayama | 604/385.28 |
| 6,350,256 B1 | * | 2/2002 | Palumbo et al. | 604/339 |
| 6,395,955 B1 | * | 5/2002 | Roe et al. | 604/361 |

FOREIGN PATENT DOCUMENTS

| | | | |
|---|---|---|---|
| JP | 2-174845 A | | 7/1990 |
| JP | 15921/1992 | | 2/1992 |
| JP | 5-86320 U | | 11/1993 |
| JP | 6-5614 U | | 1/1994 |
| JP | 31723/1994 | | 4/1994 |
| JP | 10-192339 A | | 7/1998 |
| JP | 3012472 B2 | | 12/1999 |
| JP | 2000-24030 A | | 1/2000 |
| JP | 3327939 B2 | | 7/2002 |
| JP | 2002-291802 A | | 10/2002 |
| JP | 2002291802 | * | 10/2002 |
| JP | 2002291802 | * | 10/2008 |

* cited by examiner

*Primary Examiner*—Tatyana Zalukaeva
*Assistant Examiner*—Ilya Y Treyger
(74) *Attorney, Agent, or Firm*—Sughrue Mion, PLLC

(57) ABSTRACT

In a disposable absorbent article structured such that an article body is composed of at least a top sheet arrange in a front face side, a back sheet arranged in a back face side and an absorber interposed between both of top sheet and back sheet, and a feces pocket is provided in a hip contact portion of the article body, wherein an opening portion of the feces pocket is covered with a mesh sheet.

7 Claims, 19 Drawing Sheets

(A)

(B)

(A)

(B)

(A)

(B)

(C)

(D)

ABSORBENT ARTICLE

FIELD OF THE INVENTION

The present invention relates to a disposable absorbent article such as a disposable diaper, a training pants for a baby, an incontinence pad or the like, and more particularly to an disposable absorbent article preventing an excrement such as an urine, a feces or the like, particularly loose feces from turning back and soiling a skin of a wearer.

DESCRIPTION OF THE RELATED ART

The absorbent article is generally structured such that an article body is composed of at least a liquid permeable top sheet arranged in a front face side, a liquid impermeable back sheet arranged in a back face side, and an absorber interposed between both the top sheet and the back sheet, and the excrement is absorbed and held in the absorber through the top sheet.

Conventionally, as the absorbent article, for the purpose of reserving and holding the excrement particularly the feces, there has been generally known an absorbent article providing a feces reservoir portion (hereinafter, refer to as "feces pocket"), which stores and holds the feces in a region of the article body contacting with a hip of the wearer, specifically a position of the absorber contacting with an anus outlet of the wearer.

For example, in Japanese Unexamined Utility Model Publication No. 5-86320, there is proposed a disposable diaper structured such that a feces pocket is composed of a concave portion concaved from an upper surface of an absorber, and a protruding portion defining a peripheral edge of the concave portion. Further, in Japanese Patent No. 3012472, there is proposed a disposable diaper structured such that a feces pocket is formed in an upper layer portion of an absorber composed of two layers comprising an upper layer and a lower layer.

However, each of these absorbent articles, that is, the disposable diapers can prevent the excrement from leaking out in an outer peripheral direction of the feces pocket, however, since an opening portion of the feces pocket is exposed, therefore, there is a disadvantage that the excrement stored and held in the feces pocket is in contact with the skin of the wearer so as to soil the skin directly or due to a back flow. Particularly, if the absorbent article is shifted from a predetermined position by a body pressure, a motion or the like of the wearer, the soil caused the excrement is expanded. When such a state continuous long time, there is a case that dermatitis, skin irritation or the like is generated, and there is a problem that it is very laborious for a caregiver to clean up after.

Accordingly, conventionally, in order to prevent the excrement from being in contact with the skin, Japanese Patent No. 3327939 proposes an absorbent article structured such that a feces pocket is composed of absorber of plural layers, and a pocket-like space for putting the excrement through and storing the excrement is formed between the absorber and a top sheet. However, in the absorbent article described in Japanese Patent No. 3327939, since the feces pocket is composed of absorber of the plural layers, composition is complicate and manufacturing cost is increased. In addition, since the excrement is stored in the pocket-like space via the opening portion, there still has been a concern that the excrement turns back from the opening portion due to the body pressure and the motion of the wearer.

On the other hand, in Japanese Unexamined Utility Model Publication No. 6-5614, as shown by a cross sectional view in FIG. 1, there is proposed a disposable absorbent article structured such that an article body 4 is composed of a liquid permeable top sheet 1, a liquid impermeable back member 2, and an absorber 3 interposed between the top sheet 1 and the back sheet 2, and a concave-like feces pocket 5 is provided in a hip contact portion of the article body 4, in which an opening portion 6 of the feces pocket 5 is covered with a valve portion 8 formed with extending the liquid permeable top sheet 1 having an open hole 7 in the center in a center direction of the opening portion 6. However, even in the absorbent article described in Japanese Unexamined Utility Model Publication No. 6-5614, since the open hole 7 for storing the excrement in inside is provided in the center of the feces pocket 5, it is hard to securely prevent the excrement from turning back from the open hole 7.

Further, for example, as shown in Japanese Unexamined Patent Publication No. 2000-24030, in a packed state at a time of a product (hereinafter, refer to as "product state"), such an absorbent article is frequently folded small into three or more in a longitudinal direction of the article body in order to easily handle a packing package or to reduce occupation space. Further, the absorbent article folded as mentioned above is frequently compressed strongly in a thickness direction in order to more reduce packing capacity, and thereby a fold set or a wrinkle is formed in the absorbent article.

However, as mentioned above, if the absorbent article provided with the feces pocket is folded into three or more as mentioned above, it is generated the wrinkle since the fold set reaches to the feces pocket, whereby the feces pocket is deformed. Therefore, since the excrement is hard to shift to the feces pocket from the top sheet, and since a volumetric capacity of the feces pocket becomes smaller, the excrement is hard to be stored, thereby causing a problem that the excrement leaks out in an outer peripheral direction of the feces pocket. Thus, an effect of providing the feces pocket has not been fully obtained.

DISCLOSURE OF THE INVENTION

The present invention is made by taking the mentioned above condition into consideration, and an object of the present invention is to provide a disposable absorbent article which securely absorbs and holds an excrement, particularly loose feces inside, and prevents the excrement from turning back and soiling a skin of the wearer due to a body pressure and a motion of a wearer.

The object of the present invention can be achieved by a disposable absorbent article structured such that an article body is composed of at least a top sheet arranged in a front face side, a back sheet arranged in a back face side, and an absorber interposed between the top sheet and the back sheet, and a feces pocket storing and holding an excrement is provided in a hip contact portion of the article body, wherein the absorbent article is formed in a shape folded into two in a longitudinal direction of the article body in a product state, wherein an opening portion of the feces pocket is formed such that the opening portion of the feces pocket does not reach folded portion formed by folding into two, and wherein the opening portion of the feces pocket is covered with a mesh sheet.

Further, the object of the present invention can be effectively achieved by an absorbent article, wherein the opening portion of the feces pocket is covered with the mesh sheet and the top sheet.

Further, the object of the present invention can be more effectively achieved by an absorbent article, wherein mesh formation is performed in the top sheet at least at a position covering the opening portion of the feces pocket, and a mesh region is formed in the top sheet.

Further, the object of the present invention can be more effectively achieved by an absorbent article, wherein the opening portion of the feces pocket is covered only with the mesh sheet.

Further, the object of the present invention can be effectively achieved by an absorbent article, wherein an open area ratio of the mesh sheet and the mesh region of the top sheet is between 15 and 30%.

Further, the object of the present invention can be more effectively achieved by an absorbent article, wherein a cross sectional shape of the opening portion of the feces pocket is formed in a broadened shape toward the front face side of the article body.

Further, the object of the present invention can be more effectively achieved by an absorbent article, wherein the mesh sheet is made of water repellent material, and a region having high hydrophilic nature is formed by coating at least in a portion around the urinate outlet contacting portion of the water repellent material with hydrophilic agent.

Further, the object of the present invention can be more effectively achieved by an absorbent article, wherein the absorbent article is a tape type disposable diaper having fastening tapes and a frontal tape, the fastening tapes have one end portion pasted to end portion of a dorsal side region of the article body and other end portion provided hook member, the frontal tape is pasted to outer face of a ventral side region of the article body, and the fastening tapes is fastened to the frontal tape, and thereby the absorbent article is worn.

EFFECT OF THE INVENTION

As mentioned above, since the absorbent article in accordance with the present invention is structured such that the opening portion of the feces pocket is covered with the mesh sheet, the excrement, particularly the loose feces, stored in the inside of the feces pocket through the mesh sheet is completely isolated from the skin of the wearer by the mesh sheet. Accordingly, as the absorbent article in accordance with the present invention, since it is possible to prevent the excrement from tuning back due to the body pressure and the motion of the wearer and keep the skin of the wearer purity, it is sanitary and there is advantage that cleaning up after is easily.

Particularly, in accordance with the absorbent article structured such that the opening portion of the feces pocket is covered only with the mesh sheet, it is possible to improve an absorbability of the excrement. And in addition, since a used area of the mesh sheet material, that is, a used amount of the mesh sheet material is reduced, it is possible to reduce a manufacturing cost.

Further, in accordance with the absorbent article structured by using the mesh sheet in which the open area ratio is between 15 and 30%, preferably between 18 and 20%, it is possible to keep a best state the absorbability of the excrement, and it is possible to suppress the flowback of the excrement to a minimum.

Further, in accordance with the absorbent article structured such that the cross sectional shape of the opening portion of the feces pocket is formed in the broadened shape toward the front face side of the article body, there is advantages that it is easy to store the excrement inside the feces pocket, and that the structure is realism from the viewpoint of an operation.

Furthermore, since the absorbent article in accordance with the present invention, particularly the tape type disposable diaper, is made in the shape folded into two in the longitudinal direction of the article body in the product state, even when the fold set is formed in the folded portion, the fold set does not reach the feces pocket. Accordingly, the wrinkle is not formed in the feces pocket, and the feces pocket is not deformed. Therefore, it is possible to prevent the excrement from leaking out in the outer peripheral direction of the feces pocket.

DESCRIPTION OF THE PREFERRED EMBODIMENT

Hereinafter, the contents of the present invention will be described on the basis of preferable embodiments. In this case, the present invention is not necessarily limited to the following embodiment, it goes without saying that the structure be changed variously within a purview not departing from the scope of claims.

Figure 1:
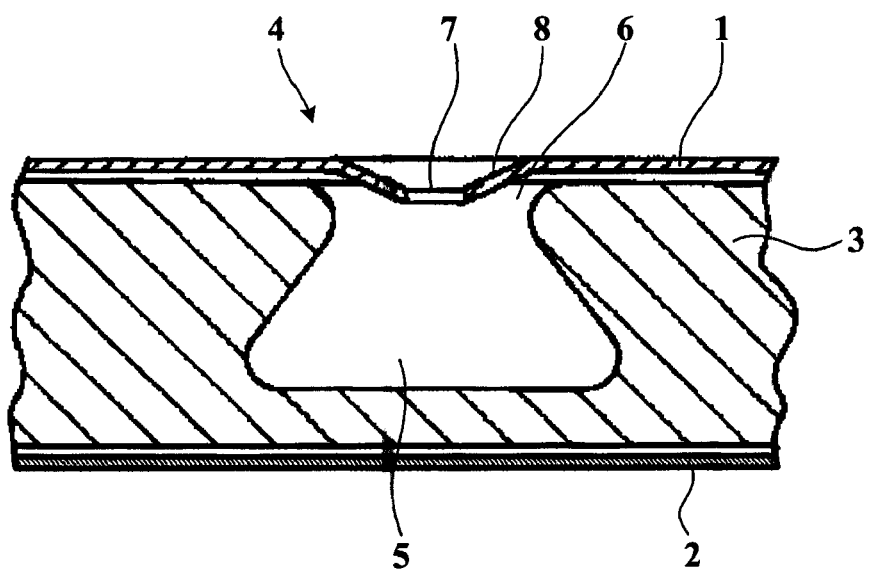
FIG. 1 is a cross sectional view showing a structure of a feces pocket in a conventional absorbent article.
Figure 2:
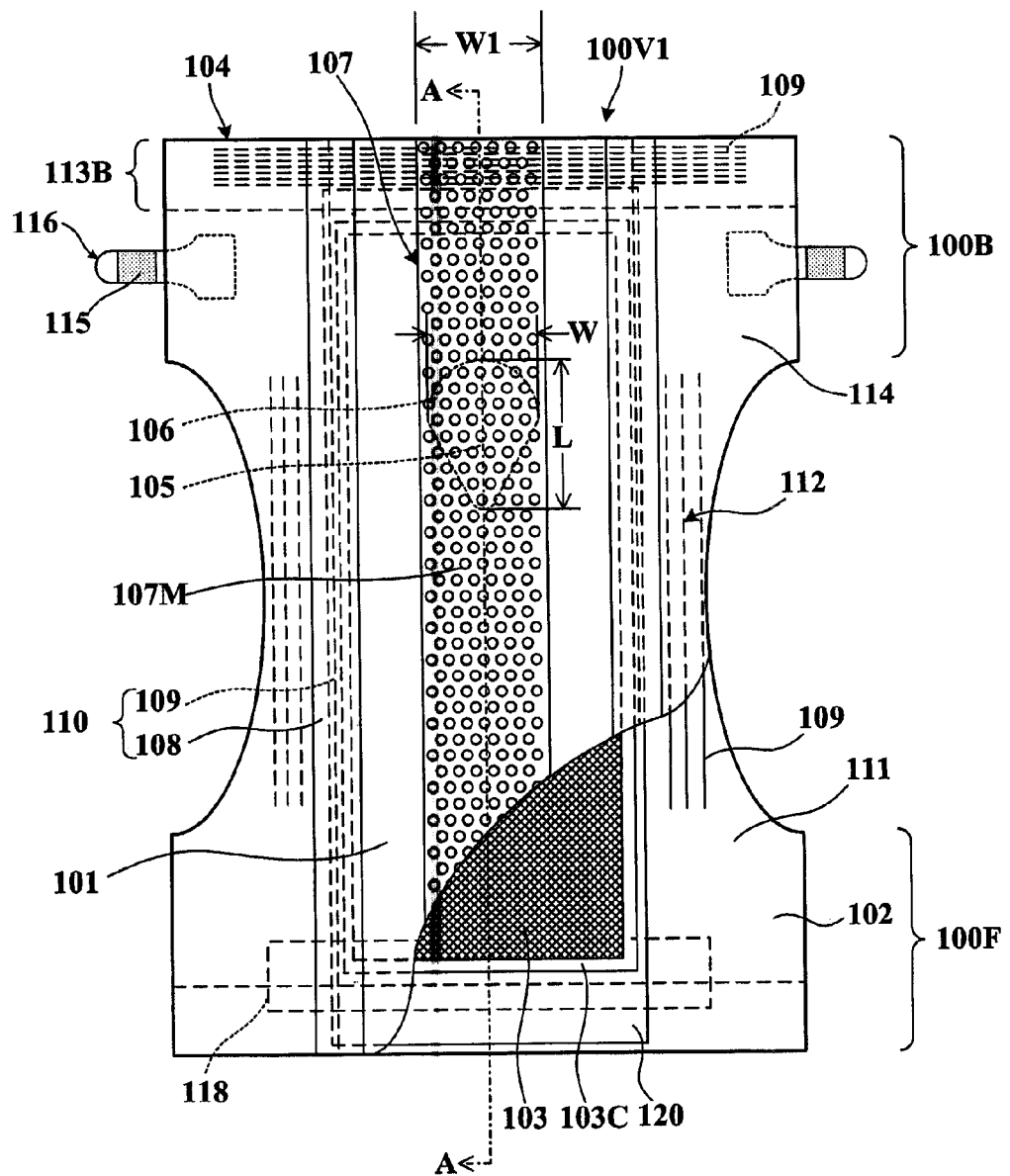
FIG. 2 is an expansion plan view of a tape type disposable diaper in accordance with a first embodiment of the present invention.
Figure 3:
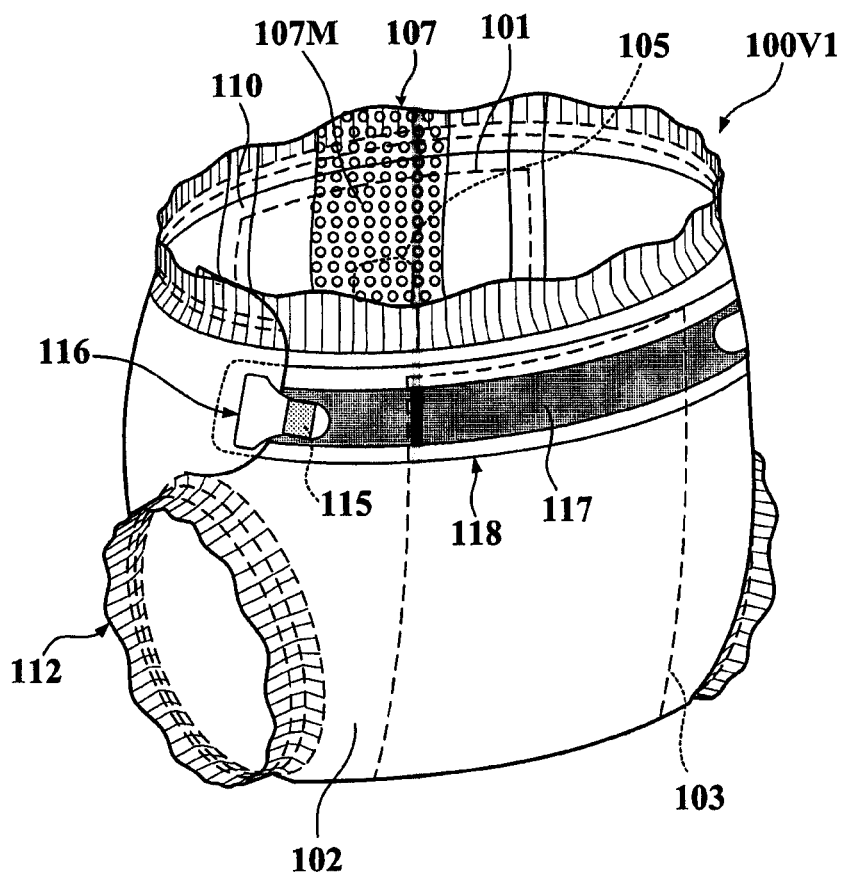
FIG. 3 is a perspective view of the diaper shown in FIG. 2 at a time of being used.

FIG. 2 is a plan view of a tape type disposable diaper (hereinafter, refer to as "present diaper") 100V1 corresponding to a first embodiment of an absorbent article of the present invention when the present diaper 100V1 is expanded and as seen from a front face side (a skin contact surface side). And FIG. 3 is a perspective view of the present diaper 100V1 at a time of being used.

As shown in FIG. 2, the present diaper 100V1 is structured such that a diaper body 104 is composed of a top sheet 101 arranged in a front face side, a back sheet 102 arranged in a back face side, and an absorber 103 interposed between both the sheets 101 and 102, and a feces pocket 105 storing and holding an excrement is provided at a hip contact position of the diaper body 104, specifically a position of the absorber 103 where an anus outlet of a wearer is positioned. An upper surface of an opening portion 106 of the feces pocket 105 is covered with a rectangular mesh sheet 107 extending in a longitudinal direction of the diaper body 104 and pasting on an upper surface of the top sheet 101.

A planar shape of the diaper body 104 is formed in a sand glass-like shape, and a three-dimensional gather 110 is formed in a longitudinal direction of both side edges of the absorber 103. The three-dimensional gather 110 is risen up to the front face side by a gather sheet 108 provided in the front face side, and an elastic stretching member 109 arranged along an inner end edge of the gather sheet 108. A side flap portion 111 in which the absorber 103 is not interposed is formed with the back sheet 102 portion extending to a side portion from a side edge of the absorber 103, and an outer sheet portion of the three-dimensional gather sheet 108. And a crimp-shaped plane gather 112 is formed in the side flap portion 111, by arranging a plurality of elastic stretching members 109 between the outer sheet portion of the three-dimensional gather sheet 108 and the backsheet 102 portion so as to be along the longitudinal direction of the diaper body 104.

A plurality of elastic stretching members 109 is arranged in a width direction of a dorsal side region 100B of the present diaper 100V1, whereby an end flap portion 113B is formed. Further, a fastening tape 116 is coupled, and the fastening tape 116 provide with hook member 115 to right and left protruding portions in the dorsal side region 100B of the diaper body 104, that is, an end portion in a width direction of a side panel portion 114. Furthermore, a rectangular frontal tape 118 having loop member 117 in a front face is pasted to a ventral side region 100F in the back face side, that is, the back sheet 102 of the ventral side region 100F. As shown in FIG. 3, the hook member 115 of the fastening tape 116 is mechanically engaged with the loop member 117 of the frontal tape 118, whereby the fastening tape 116 is fastened to the frontal tape 118, and thus the present diaper 100 is worn. In this case, to the front face of the frontal tape 118, there may be printed a design comprising a fastening position mark indicating a fastening position of the fastening tape 116 or a babies' favorite image such as an animal, and so on, as needed.

Figure 4:
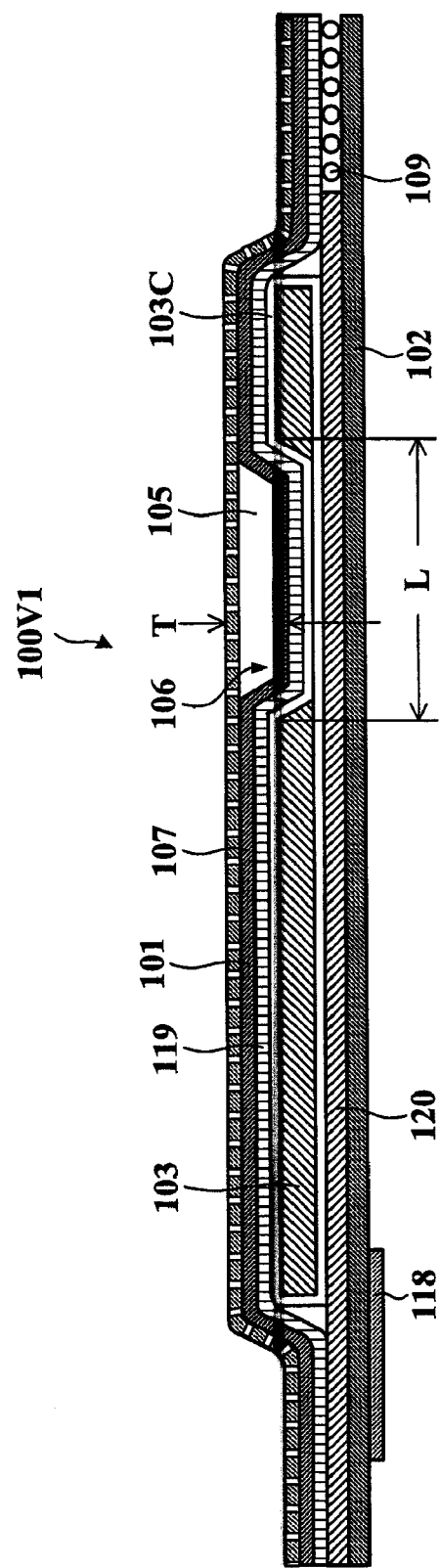
FIG. 4 is a cross sectional view along a line A-A in FIG. 2.

FIG. 4 is a cross sectional view along a line A-A in FIG. 2. As shown in FIG. 4, in the present diaper 100V1, a second sheet 119 is arranged between the top sheet 101 and the absorber 103, and a waterproof film 120 is arranged between the back sheet 102 and the absorber 103. In this case, since the second sheet 119 and the waterproof film 120 are appropriately provided as needed, they may be omitted.

In the present diaper 100V1, as a constituent material of the top sheet 101 and the second sheet 119, it is possible to preferably employ a material having a liquid permeability and a hydrophilic nature such as an imperforated or perforated unwoven fabric, a porous plastic sheet or the like. As a material fiber constituting the unwoven fabric, it is possible to employ, for example, a synthetic fiber such as an olefin family such as polyethylene, a polypropylene or the like, polyester family, amide family or the like, in addition, a regenerated fiber such as a rayon, a cupra or the like, and a natural fiber such as a cotton or the like. Further, it is possible to effectively employ a compound fiber such as a core sheath type fiber having a fiber of a high melting point as a core and having a fiber of a low melting point as a sheath, a side-by-side type fiber, a divided type fiber or the like. With regard to a processing method, it is possible to employ an unwoven fabric obtained by an appropriate processing method such as a spun lace method, a spun bond method, a thermal bond method, a melt blown method, a needle punch method or the like. Among these processing methods, the spun lace method is excellent in a point of flexibility and draping characteristic, and the thermal bond method is excellent in a point that an unwoven fabric is bulky and soft. However, the top sheet 101 in the present diaper 100V1 is not necessarily limited to these materials or processing methods.

As the back sheet 102 and the waterproof film 120, it is possible to preferably employ liquid impermeable material composed of a plastic sheet such as a polyethylene, a polypropylene or the like, an unwoven fabric or the like, or the similar material thereto. In addition, for example, a melt blown composed of a polypropylene or a polyolefin copolymer or a film material can be also employed. As an example of the copolymer, there are an ethylene vinyl acetate, an ethylene methyl acetate, an ethylene ethyl acrylate, a polyvinyl chloride or the like. Further, a single spun bonded layer composed of the mentioned above each materials, two layers composed of the spun bonded material and the melt blown material, and the like can be also employed. It is possible to give a cloth-like touch feeling to the back sheet 102 by using such a spun bonded material. In this case, from the viewpoint of the preventing a stuffy state, a sheet material having an air permeability and a moisture permeability apply to the back sheet 102, in addition to the material having the liquid impermeability. As such sheet material, a micro porous sheet is preferably used. The micro porous sheet is obtained by drawing in uniaxial direction or biaxial direction after a sheet is formed by melting and mixing an inorganic filler in an olefin family resin such as a polyethylene, a polypropylene or the like. The sheet material having the liquid impermeability, the air permeability and the moisture permeability is preferably used particularly for the waterproof film 120.

As the absorber 103, it is possible to employ the various absorbers if the absorber absorb and hold the excrement (particularly, a body fluid such as a water or the like contained in an urine or a feces). However, in general, from the viewpoint of the absorption function and the cost, absorber, which is formed by mixed the absorbable polymer powder in the fluff-like pulp, is preferable employed. As such pulp, the one composed of a cellulose fiber such as a chemical pulp obtained from a wood, a molten, pulp or the like, or an artificial cellulose fiber such as a rayon, an acetate or the like can be used. Among these pulps, from the viewpoint of the function and the cost, the soft wood pulp having a longer fiber length than a hard wood pulp is more preferably employed. The absorber 103 in the present diaper 100 is wholly wrapped by a water absorption paper 103C such as a crepe paper or the like for the purpose of keeping a shape, quickly diffusing the excrement (particularly the body fluid such as the water or the like contained in the urine and the feces) and preventing the once absorbed excrement from turning back. And the plane shape of the absorber 103 is formed in a rectangular shape. In this case, the water absorption paper 103C may be omitted due to a purpose or a way of use of the diaper itself. And the plane shape of the absorber 103 may be changed in design to an any shape such as the sand glass-like shape similar to the diaper body 104, an oval shape, a gourd shape or the like. As mentioned above, the feces pocket 105 is provided on the hip contact portion of the absorber 103, and details thereof will be described later.

The mesh sheet 107 employs a soft touch sheet material formed with an unwoven fabric or a plastic film, or by laminating these materials to make a thickness between 0.1 and 5.0 mm, preferably between 0.3 and 2.0 mm, and a minute net-shaped mesh (aperture) region 107M is formed on a whole surface of the sheet material in accordance with a pin emboss process, a suction method or the like which are well known in this field.

An aperture ratio of this mesh region 107M is made between 15 and 30%, preferably made between 18 and 20%, and a number of apertures is made to be equal to or less than 15 per $cm^2$, preferably made between 6 and 12 per $cm^2$. Further, a size of the aperture is made between 0.1 and 11.0 mm in diameter, preferably between 0.15 and 5.5 mm in diameter. In this case, a hydrophilic nature of a front face of the mesh sheet 107 is preferably made to between a regular hydrophilic nature which the degree of hydrophilic nature is low, and a water repellant nature. If the hydrophilic nature is too high, the excrement, particularly the water of the loose feces is diffused to the front face. Therefore, since the expansion of the water is visible from the wearer even if a solid of the feces is absorbed, it is not desirable that it gives an uncomfortable feeling. Further, the plane shape of the mesh (the aperture) is not limited to a circular shape, but can employ an ellipse shape and any other shapes.

Here, an improvement of the absorbability of the body fluid such as the water or the like contained in the urine or the feces of the diaper 100V1, and an improvement of a spot absorbability of the solid or the like of the feces are that two contradict natures such as the hydrophilic nature of the mesh sheet 107 and the water repellent nature of the mesh sheet 107 is improved both. Further, since a best balance of the contradict natures such as the absorbability of the body fluid and the spot absorbability in the mesh sheet 107 is different depending on a growth degree of the wearer, that is, the size of the diaper 100V1, it is necessary to adjust the best balance.

As a method of giving the water repellent nature and the regular hydrophilic nature to the mesh sheet 107 as mentioned above, it is preferable to employ a method of giving the hydrophilic nature to the mesh sheet 107 by coating the mesh sheet 107 having the water repellent nature with a hydrophilic agent on a manufacturing line of the diaper 100V1. The mesh sheet 107 is required the different degree of the hydrophilic nature depending on the size of the diaper 100V1. However, even the mesh sheet 107 of the same lot, it is possible to appropriate adjust the degree of the hydrophilic nature depending on the size of the diaper 100V1. Therefore, in the case of manufacturing the plural sizes of diapers 100V1, it is not necessary to use the mesh sheets 107 of a small lot having the degree of the hydrophilic nature corresponding to a specific size of the diaper 100V1, so that it is possible to reduce the manufacturing cost. In this case, as the hydrophilic agent, known various materials such as an alkyl phosphate ester or the like can be employed, and as the method of coating the hydrophilic agent, known various methods such as a spray dispersion, a roll transcription or the like can be employed.

Further, in the case of giving the hydrophilic nature by coating the mesh sheet 107 having the water repellent nature with the hydrophilic agent, it is possible to intermittently coat the hydrophilic agent. Therefore, the degree of the hydrophilic nature can be easily varied appropriately in depending on the position of each of the diapers 100V1. That is, for example, the portion around the feces pocket portion, in which the high spot absorbability is required, may be left being water repellent nature without coating with hydrophilic agent, or may be made the regular hydrophilic nature by coating a small amount of hydrophilic agent, while the portion around the urinate outlet, in which the high absorbability of body fluid is required, may be made the high degree of the hydrophilic nature by coating a lot of hydrophilic agent. Accordingly, it is possible to reduce the generation of the skin irritation or the like.

In this case, it is not limited in the case that the degree of the hydrophilic nature and the degree of the water repellent nature of the mesh sheet are adjusted by coating a hydrophilic agent to the mesh sheet 107 having the water repellent nature as mentioned above, and in addition to this, in the same manner, it is possible that the degree of the hydrophilic nature and the degree of the water repellent of the mesh sheet 107 are adjusted by coating the mesh sheet 107 having the hydrophilic nature with a water repellent agent.

As the gather sheet 108 forming the three-dimensional gather 110, an unwoven fabric of the water repellent nature, a plastic film or the like is effective in a point of preventing the excrement from leaking. Therefore, as the gather sheet 108, it is possible to select a material having such that nature, or a material to which such the nature is giving by processing.

A filamentous elastic rubber is generally applied for the elastic stretching member 109. As such rubber material, it is possible to employ a material such as a styrene family rubber, an olefin family rubber, an urethane family rubber, an ester family rubber, a polyurethane, a polyethylene, a polystyrene, a styrene butadiene, a silicone, a polyester or the like. In this case, the forming material of the stretching member 109 is not necessarily limited to the material, but it is possible to known various materials having an elasticity, for example, a thermoplastic elastomer, a plastic sheet, a rubber sheet or the like. Among these materials, it is particularly preferable to employ the thermoplastic elastomer. And as the thermoplastic elastomer, it is possible to employ known various materials, for example, a styrene family elastomer, an olefin family elastomer, a polybutadiene family elastomer, a polyester family elastomer, a polyamide family elastomer, an urethane family elastomer, a vinyl chloride family elastomer, a fluorine family elastomer, an ionomer resin, a silicone family resin or the like. Further, these thermoplastic elastomer may be independently used, however, two or more kinds of these thermoplastic elastomer may be used by mixed. And among these materials, it is particularly preferable to employ a styrene family elastomer or an olefin family elastomer.

FIG. 4 is a cross sectional view along a line A-A in FIG. 2, and it shows a cross sectional structure of the feces pocket 105 in the present diaper 100V1. As shown in FIG. 2, a plane shape of the opening portion 106 of the feces pocket 105 is formed in a teardrop shape having a length L and a width W from the hip contact portion of the article body 104 (specifically the position of the absorber 103 in which the anus outlet of the wearer is positioned) toward the dorsal side region 100B, and a cross sectional shape of the opening portion 106 of the feces pocket 105 is formed with a depth T in a broadened shape toward the top sheet 101 side, that is, the front face side of the diaper body 104. An opening area S of the opening portion 106 formed in the teardrop shape in plane shape is made between 5 and 20%, preferably between 10 and 15% of a total area of the absorber 103 (at least 15 cm² for babies), and the length L and the width W are made to such values that can cover at least the anus outlet portion of the wearer and can cover even if the hip position is somewhat shifted from the original position in the longitudinal direction and the width direction.

The feces pocket 105 is formed with the depth T equal to the thickness of the absorber 103, that is, by forming a through hole in the absorber 103, and the top sheet 101 is covered and pasted on a whole surface of the feces pocket 105, and the opening portion 106 of the feces pocket 105 is covered with the mesh sheet 107. In this case, a volumetric capacity of the feces pocket 105 is made between 10 and 50 cm³ for babies, and is made between 50 and 100 cm³ for adults.

Here, it is preferable that the plane shape of the opening portion 106 is formed in a curve line rather than a straight line for preventing a wrinkle or a twist from being generated in the absorber 103. Further, it is preferable that the cross sectional shape of the openings portion 106 is formed in the broadened shape toward the front face side of the diaper body 104 as mentioned above. In accordance with this structure, the excrement excreted from the anus outlet, particularly the loose feces smoothly flows to the feces pocket 105, and the structure is realism from the viewpoint of an operation.

Since the present diaper 100V1 is structured as mentioned above, in accordance with the present diaper 100V1, the excrement excreted from the anus outlet, particularly the loose feces is stored on the upper surface of the top sheet 101 of the opening portion 106 of the feces pocket 105 through the mesh of the mesh sheet 107. At this time, the water contained in the excrement is immediately absorbed and held in the absorber 103 through the water absorption paper 103C, and the solid of the excrement is isolated from the skin of the wearer by the mesh sheet 107 provided in such a manner as to cover the opening portion 106, whereby the excrement is prevented from turning back. Further, even if the present diaper 100V1 is shifted from the predetermined position due to the body pressure, the motion or the like of the wearer, the soil is not expanded, and it is possible to always keep the hip of the wearer purity. Therefore, there can be obtained an advantage that the dermatitis or the skin irritation is not generated, and cleaning up after is very easy for a caregiver.

The subject matter of the present invention is described with regard to the first embodiment. However, the structure of the present invention can be modified to various aspects as below.

Figure 5:
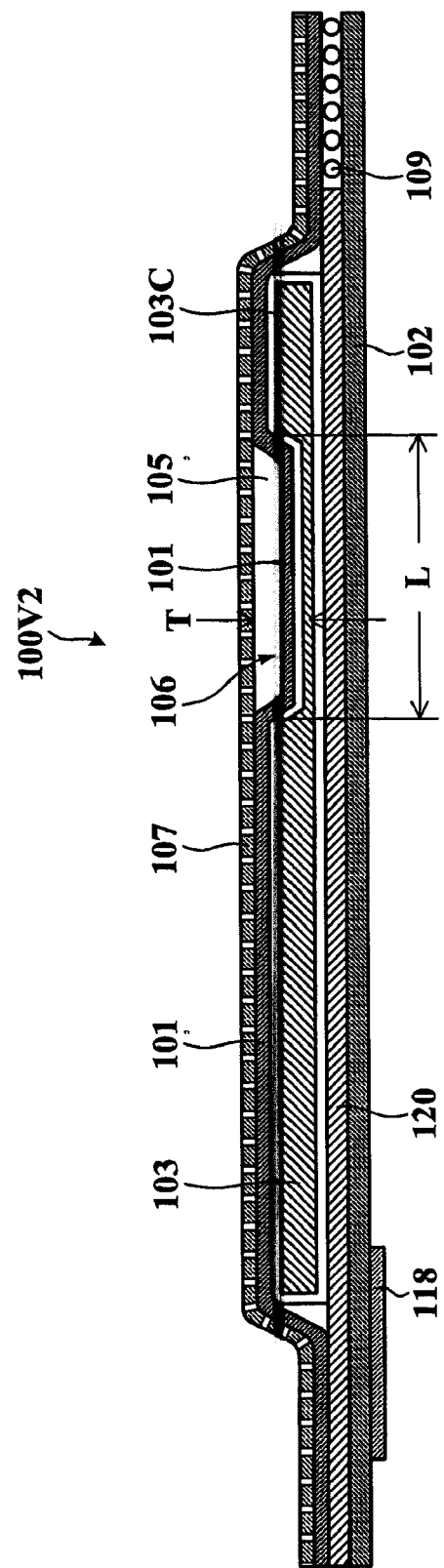
FIG. 5 is a cross sectional view of a tape type disposable diaper in accordance with a second embodiment of the present invention.

FIG. 5 is a cross sectional view of a tape type disposable diaper (hereinafter, refer to as "present diaper 100V2") in accordance with a second embodiment of the present invention. And FIG. 5 shows according as the cross sectional view of the diaper 100V1 (FIG. 4). A basic structure of the present diaper 100V2 is substantially the same as the diaper 100V1 except for an omission of the second sheet 119 and the structure of the feces pocket 105 and its periphery.

As illustrated, the present diaper 100V2 is structured such that the feces pocket 105 is provided by forming a concave portion having a depth T to a partway in the thickness direction of the absorber 103 at a predetermined position of the absorber 103, and the top sheet 101 is covered and pasted on a whole surface of this concave portion, and the opening portion 106 of the feces pocket 105 is covered with the mesh sheet 107. Even in the present diaper 100V2 in which the feces pocket 105 is formed in this manner, if the excrement is excreted, the excrement is immediately shifted to the feces pocket 105 through the mesh sheet 107. Therefore, there can be obtained an advantage that the absorbability becomes extremely good.

Figure 6:
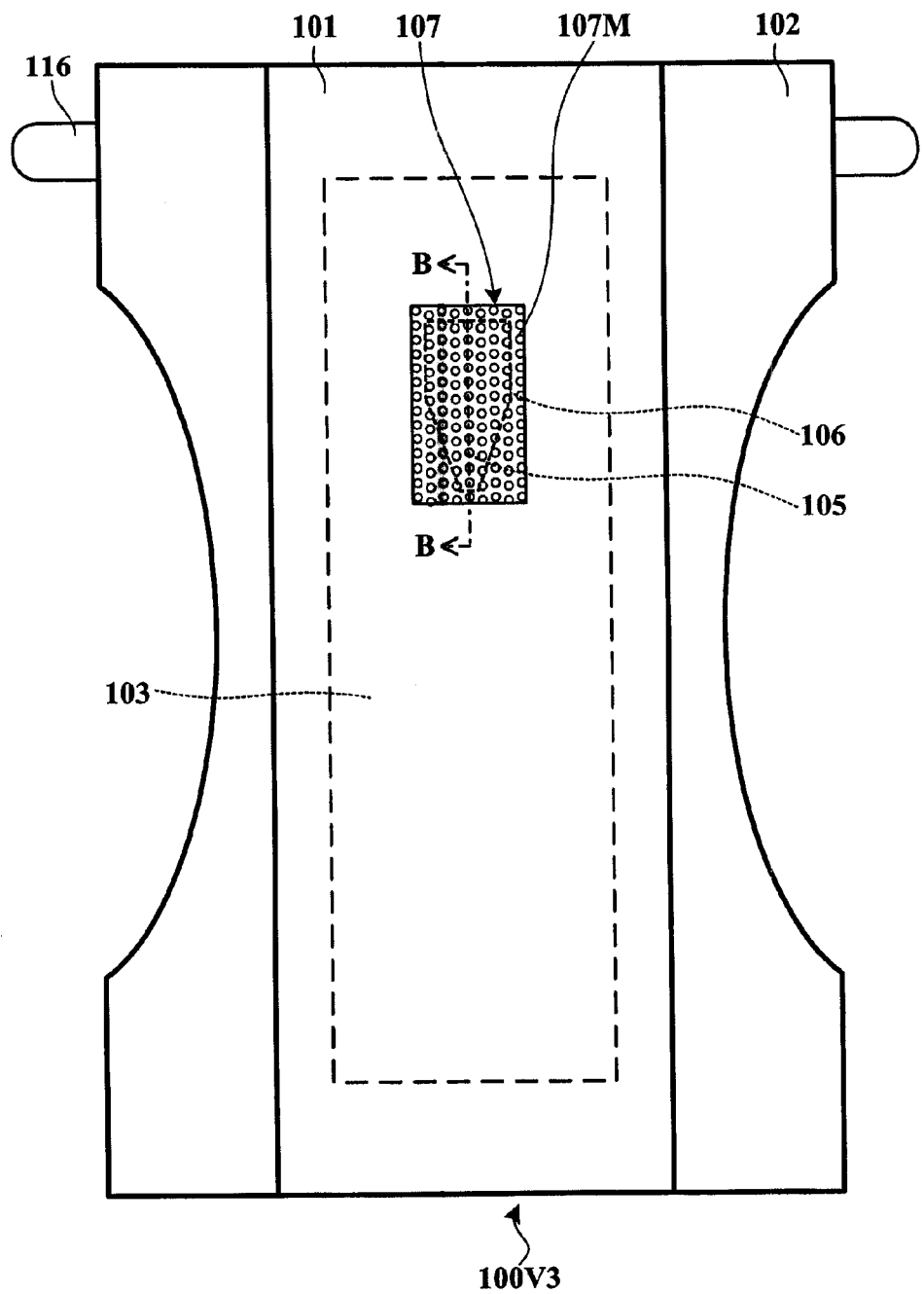
FIG. 6 is an expansion plan view of a tape type disposable diaper in accordance with a third embodiment of the present invention.
Figure 7:
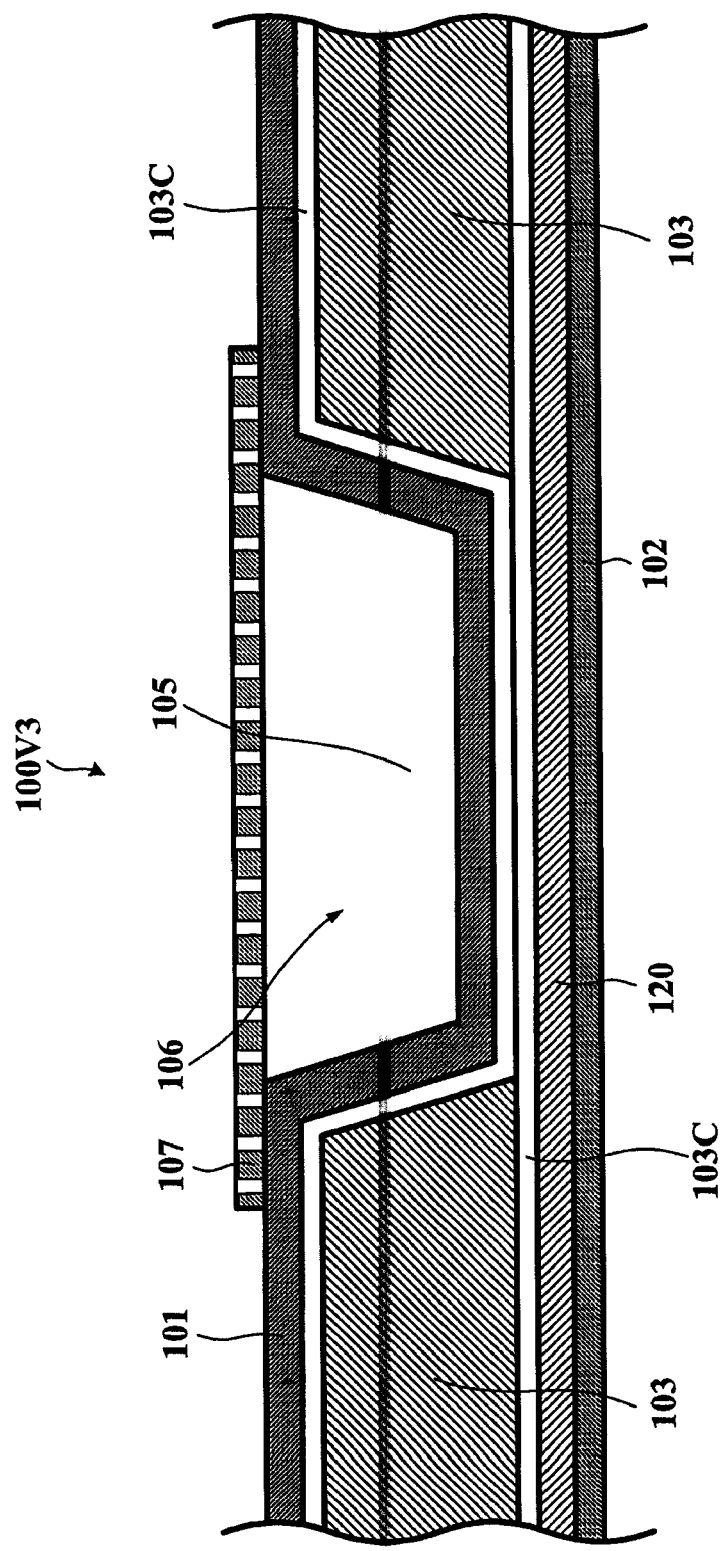
FIG. 7 is a cross sectional view along a line B-B in FIG. 6.

FIG. 6 is a plan view of a tape type disposable diaper in accordance with a third embodiment of the present invention (hereinafter, refer to as "present diaper 100V3") as seen from a front face side after the present diaper is expanded. And FIG. 7 is a cross sectional view along a line B-B in FIG. 6. In this case, a basic structure of the present diaper 100V3 is substantially the same as the diaper 100V1 except for the structure of the feces pocket 105 and its periphery, like the diaper 100V2.

The present diaper 100V3 is structured such that the mesh sheet 107 is formed in a shape (a rectangular shape in the present embodiment) and a dimension that the mesh sheet 107 can cover only the opening portion 106 of the feces pocket 105, and the mesh sheet 107 is pasted in such a manner as to cover the opening portion 106. In this manner, since the present diaper 100V3 is structured such that a used area of the mesh sheet 107, that is, a used amount of the mesh sheet 107 is made to a necessity minimum, it is possible to reduce the manufacturing cost according to the saving of the mesh sheet 107.

Figure 8:
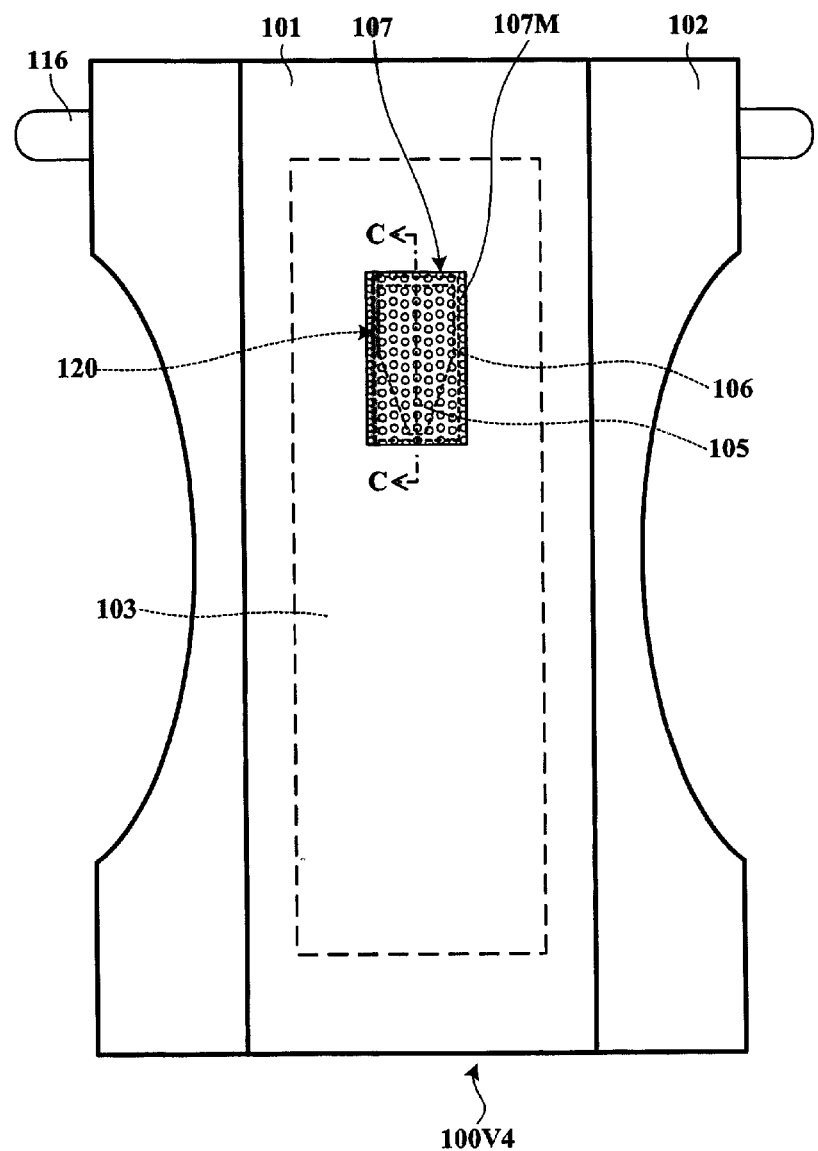
FIG. 8 is an expansion plan view of a tape type disposable diaper in accordance with a fourth embodiment of the present invention.
Figure 9:
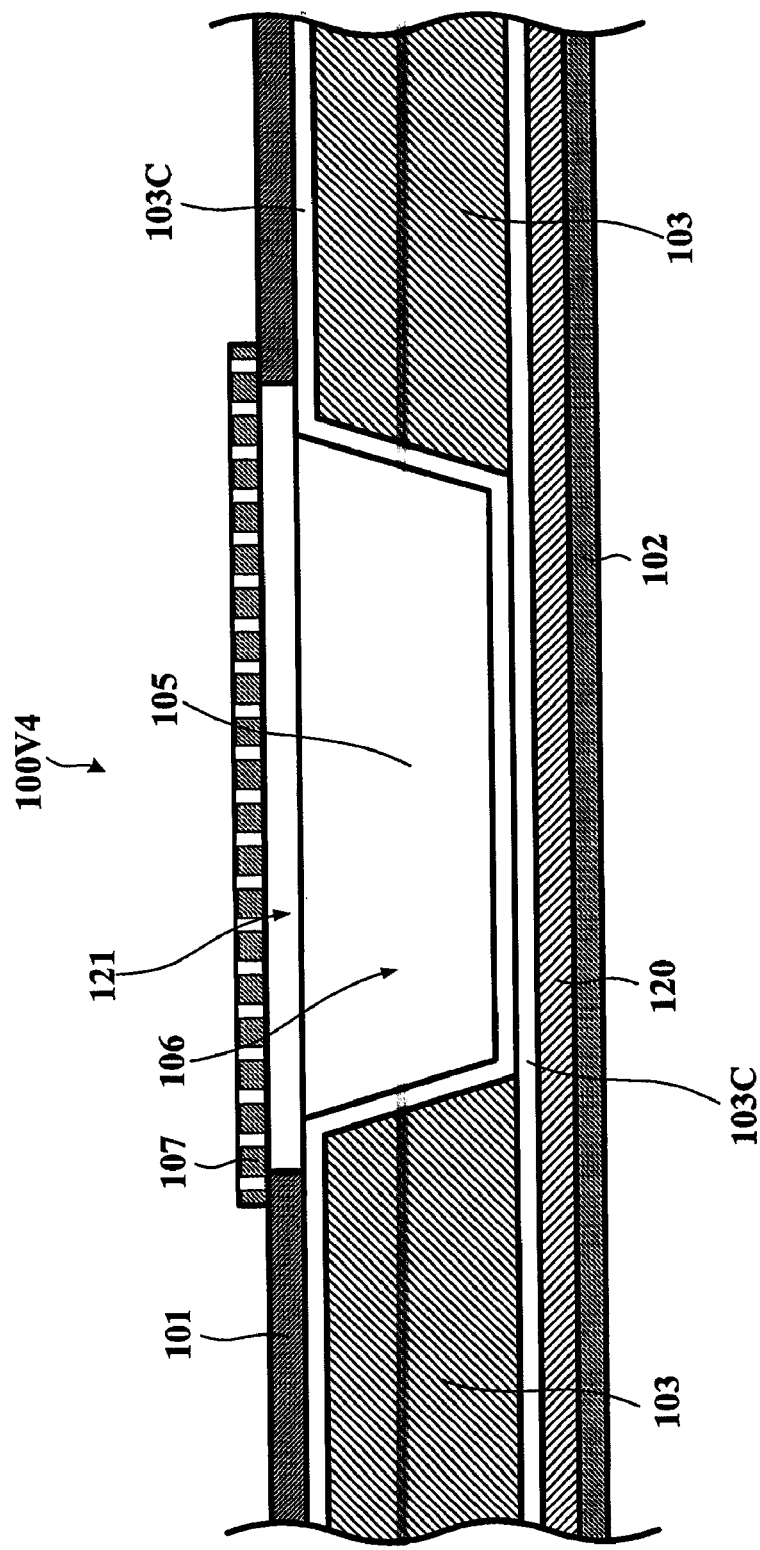
FIG. 9 is a cross sectional view along a line C-C in FIG. 8.

FIG. 8 is a plan view of a tape type disposable diaper in accordance with a fourth embodiment of the present invention (hereinafter, refer to as "present diaper 100V4") as seen from a front face side after the present diaper 100V4 is expanded. And FIG. 9 is a cross sectional view along a line C-C in FIG. 8. In this case, a basic structure of the present diaper 100V4 is also substantially the same as the diapers 100V1 to 100V3 except for the structure of the feces pocket 105 and its periphery.

The present diaper 100V4 is structured such that the mesh sheet 107 is formed in a dimension that the mesh sheet 107 can cover only the opening portion 106 of the feces pocket 105 in the same manner as mentioned above. However, in the present diaper 100V4, an opening portion 121 having an approximately similar shape with the opening portion 106 is formed in the top sheet 101, and the mesh sheet 107 is pasted in such a manner as to cover the opening portion 121 of the top sheet 101. In this manner, since the present diaper 100V4 is structured such that the opening portion 106 of the feces pocket 105 is covered only with the mesh sheet 107, the excrement is stored in the feces pocket 105 directly through the mesh sheet 107. Therefore, there can be obtained an advantage that the absorbability becomes good like the diaper 100V2 in addition to the reduction of the manufacturing cost.

Figure 10:
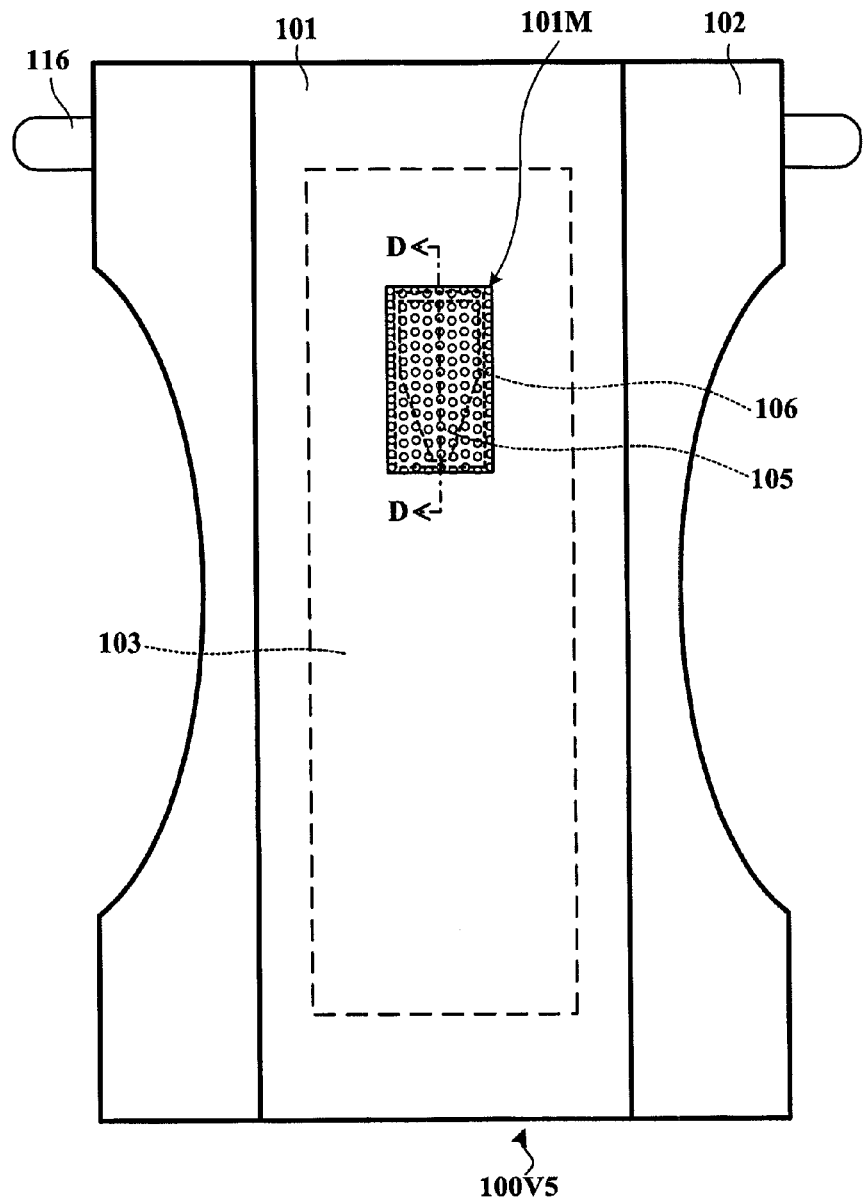
FIG. 10 is an expansion plan view of a tape type disposable diaper in accordance with a fifth embodiment of the present invention.
Figure 11:
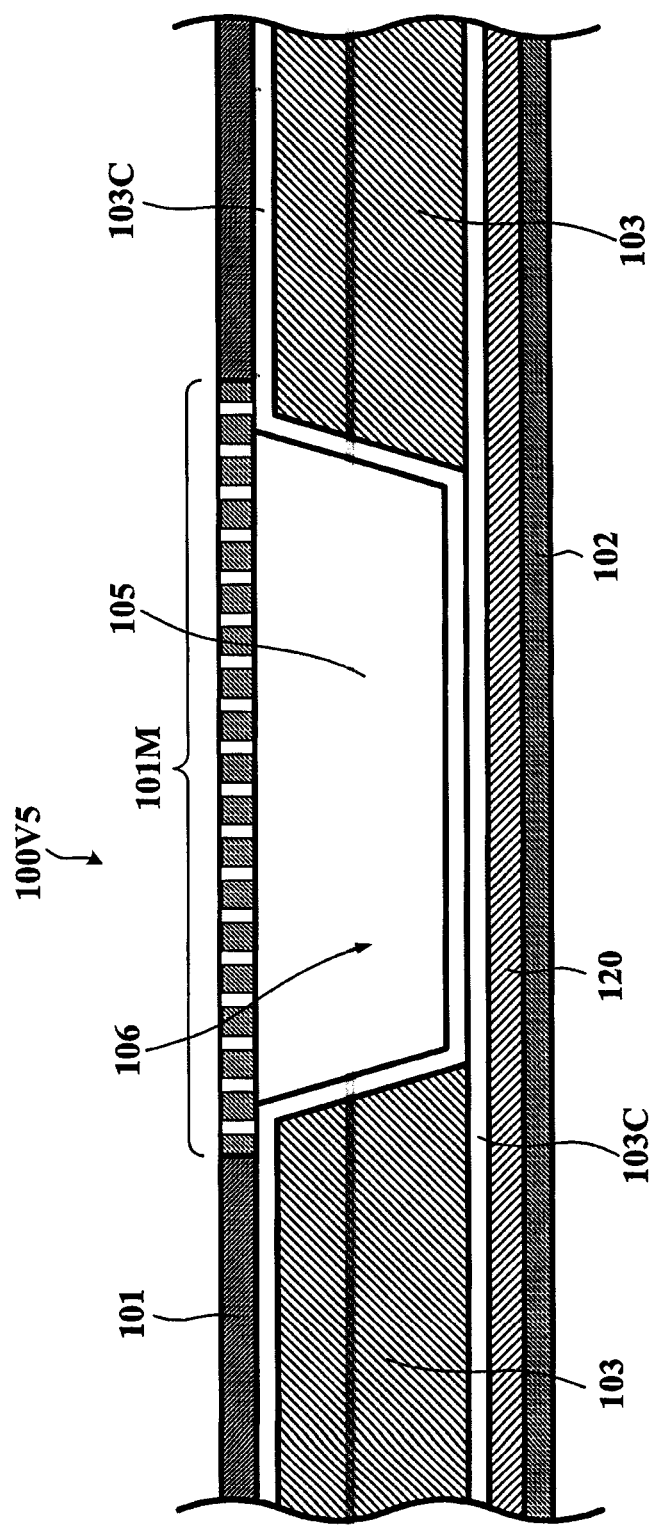
FIG. 11 is a cross sectional view along a line D-D in FIG. 10.

FIG. 10 is a plan view of a tape type disposable diaper in accordance with a fifth embodiment of the present invention (hereinafter, refer to as "present diaper 100V5") as seen from a front face side after the present diaper 100V5 is expanded. And FIG. 11 is a cross sectional view along a line D-D in FIG. 10. In this case, a basic structure of the present diaper 100V5 is also substantially the same as the diapers 100V1 to 100V4 except for the structure of the feces pocket 105 and its periphery.

The present diaper 100V5 is structured such that a mesh region 101M is formed at a position of the top sheet 101 covering the opening portion 106 of the feces pocket 105. And the present diaper 100V5 is different in structure from each of the diapers 100V1 to 100V4 in a point that the mesh sheet 107 as mentioned above is not used at all. In this case, it is possible to easily achieve the formation of the mesh region 101M in a partial region of the top sheet 101 by using the mesh forming method mentioned above. In accordance with the present diaper 100V5, since the material sheet for forming the mesh and forming the mesh itself become unnecessary. Therefore, there can be obtained an advantage that the manufacturing cost is further reduced.

Figure 12:
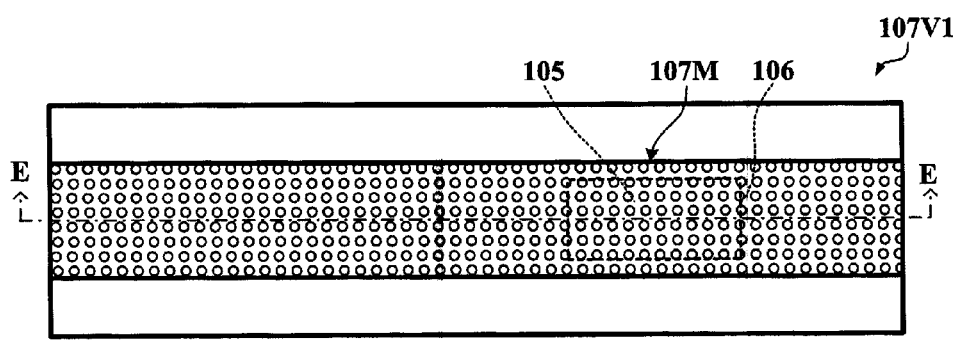
FIG. 12(A) is a plan view showing a first modified example of a mesh sheet of the present invention.
FIG. 12(B) is a cross sectional view along a line E-E in FIG. 12(A).
Figure 12:
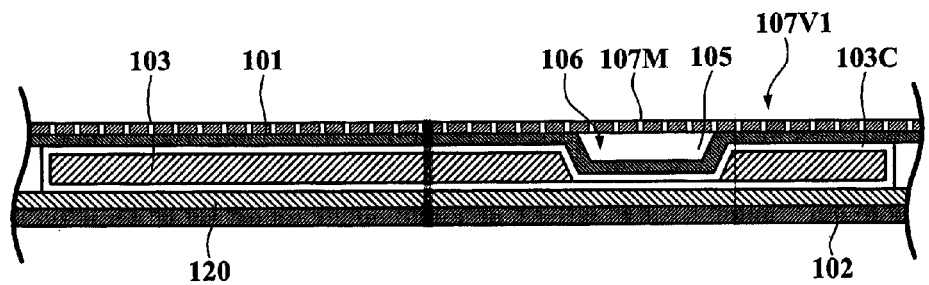
Figure 13:
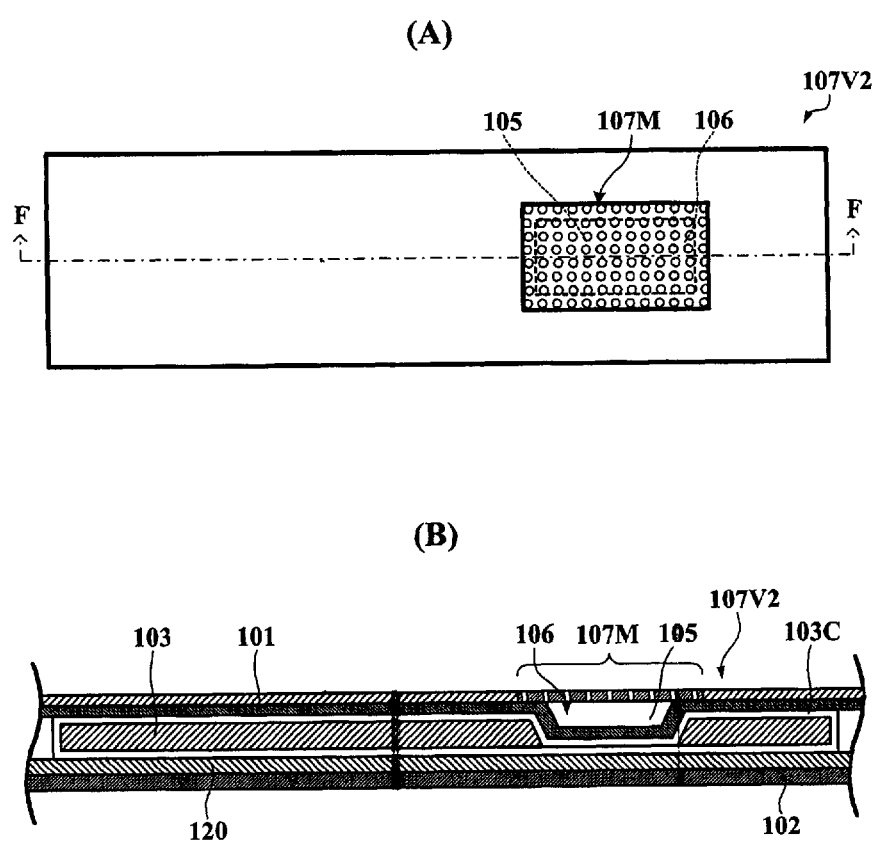
FIG. 13(A) is a plan view showing a second modified example of the mesh sheet of the present invention.
FIG. 13(B) is a cross sectional view along a line F-F in FIG. 13(A).
Figure 14:
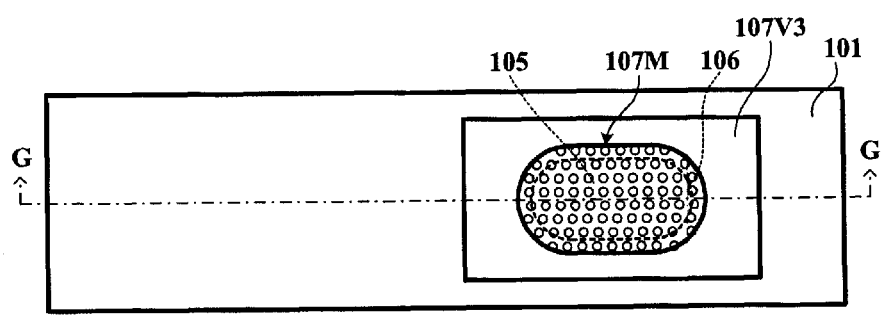
FIG. 14(A) is a plan view showing a third modified example of the mesh sheet of the present invention.
FIG. 14(B) is a cross sectional view along a line G-G in FIG. 14(A).
Figure 14:
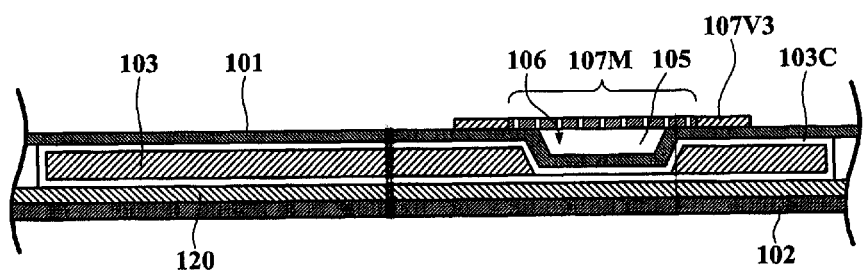

Further, in the present invention, the structure of the mesh sheet 107 can be changed to various structures, for example, as shown in FIGS. 12 to 14 showing the main portion structure of the diaper body in a plan view and a cross sectional view.

FIG. 12(A) is a plan view of a mesh sheet 107V1 in accordance with a first modified example, and FIG. 12(B) is a cross sectional view along a line E-E in FIG. 12(A). In other words, the present mesh sheet 107V1 is structured by forming a mesh region 107M over a whole region in a longitudinal direction in the center of the material sheet, that is, a direction in which the urine and the feces flow, in addition to the opening portion 106 of the feces pocket 105.

FIG. 13(A) is a plan view of a mesh sheet 107V2 in accordance with a second modified example, and FIG. 13(B) is a cross sectional view along a line F-F in FIG. 13(A). The present mesh sheet 107V2 is structured by forming the mesh region 107M in the material sheet only in a region which can over the opening portion 106 of the feces pocket 105, and forming in a rectangular shape.

FIG. 14(A) is a plan view of a mesh sheet 107V3 in accordance with a third modified example, and FIG. 14(B) is a cross sectional view along a line G-G in FIG. 14(A). The present mesh sheet 107V3 is structured by making the material sheet itself to necessity minimum shape (rectangular shape in the present example) and dimension, and forming the mesh region 107M covering the opening portion 106 of the feces pocket 105 in an approximately center of the material sheet in such a manner as to coincide with a shape of the opening portion 106 (an ellipse shape in the present example).

Each of these mesh sheets 107V1, 107V2 and 107V3 can achieve a desired purpose, however, particularly in the case of the mesh sheet 107V3, since the used amount of the material sheet and a mesh processing amount can be a little, it is advantageous in view of the manufacturing cost.

Figure 15:
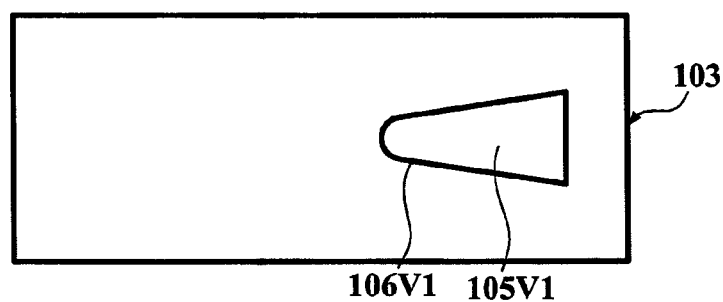
FIG. 15 is a plan view showing a modified example of a feces pocket of the present invention.
Figure 15:
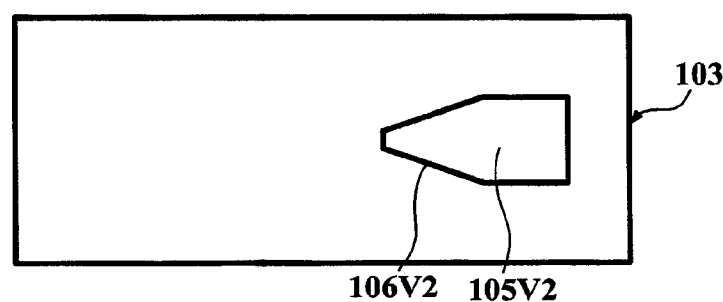
Figure 15:
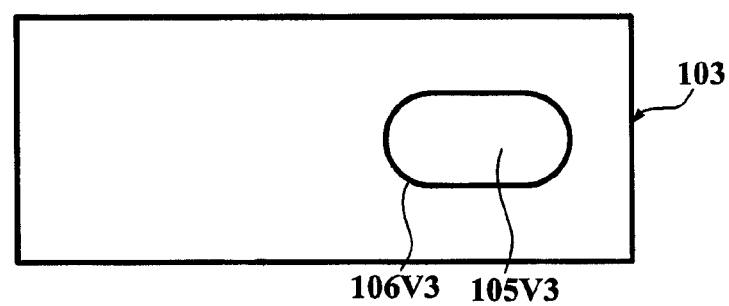
Figure 15:
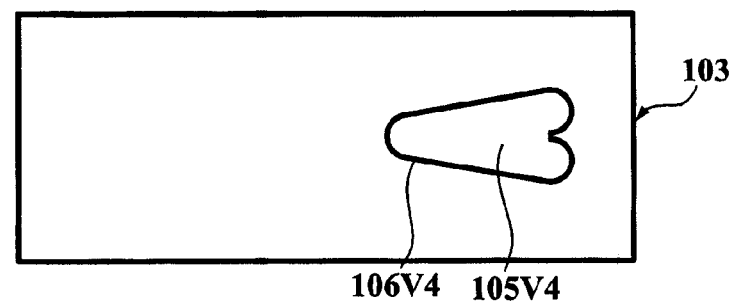
Figure 16:
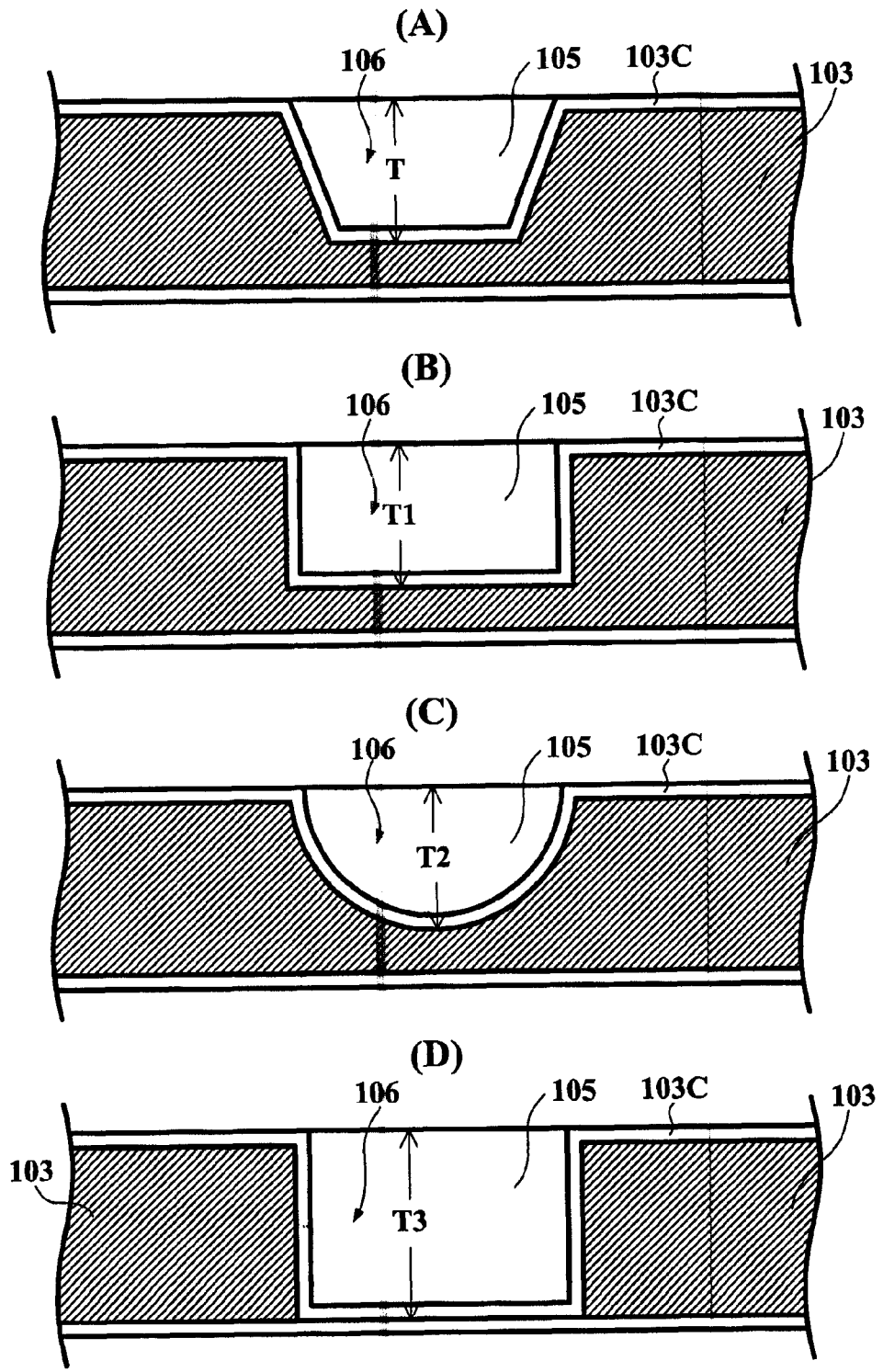
FIG. 16 is a cross sectional view showing a modified example of the feces pocket of the present invention.

Furthermore, in the present invention, it is possible to change the shape of the feces pocket 105 provided in the absorber 103 to various shapes, for example, as shown in FIG. 15 by a plane shape and in FIG. 16 by a cross sectional shape.

Specifically, a feces pocket 105V1 in accordance with a first modified example shown in FIG. 15(A) is structured such that a plane shape of an opening portion 106V1 is formed in a triangular shape expanding toward a dorsal side, a feces pocket 105V2 in accordance with a second modified example shown in FIG. 15(B) is structured such that a plane shape of an opening portion 106V2 is formed in a baseball home plate shape, a feces pocket 105V3 in accordance with a third modified example shown in FIG. 15(C) is structured such that a plane shape of an opening portion 106V3 is formed in an ellipse shape, and a feces pocket 105V4 in accordance with a fourth modified example shown in FIG. 15(D) is structured such that a plane shape of an opening portion 106V4 is formed in a heart shape expanding toward a dorsal side. In this case, as mentioned above, it is preferable that the plane shape of the opening portion 106 is formed with curve line, however, even if it is illustrated various shapes, it can be practicable.

Further, with regard to the cross sectional shape of the feces pocket 105, as shown in FIG. 16(A), it is preferable as mentioned above that the cross sectional shape is formed in the broadened shape toward the front face side of the diaper body 104 with the depth T. However, as shown in FIG. 16(B), the cross sectional shape may be formed in a rectangular shape with a depth T1 to a partway in the thickness direction of the absorber 103, as shown in FIG. 16(C), the cross sectional shape may be formed in a semispherical shape with a depth T2 to a partway in the thickness direction of the absorber 103, or as shown in FIG. 16(D), the cross sectional shape may be formed with a through hole in the absorber 103 with a depth T3 equal to the thickness of the absorber 103.

A folded aspect in a product state of the absorbent article in accordance with the present invention will be described below.

Figure 17:
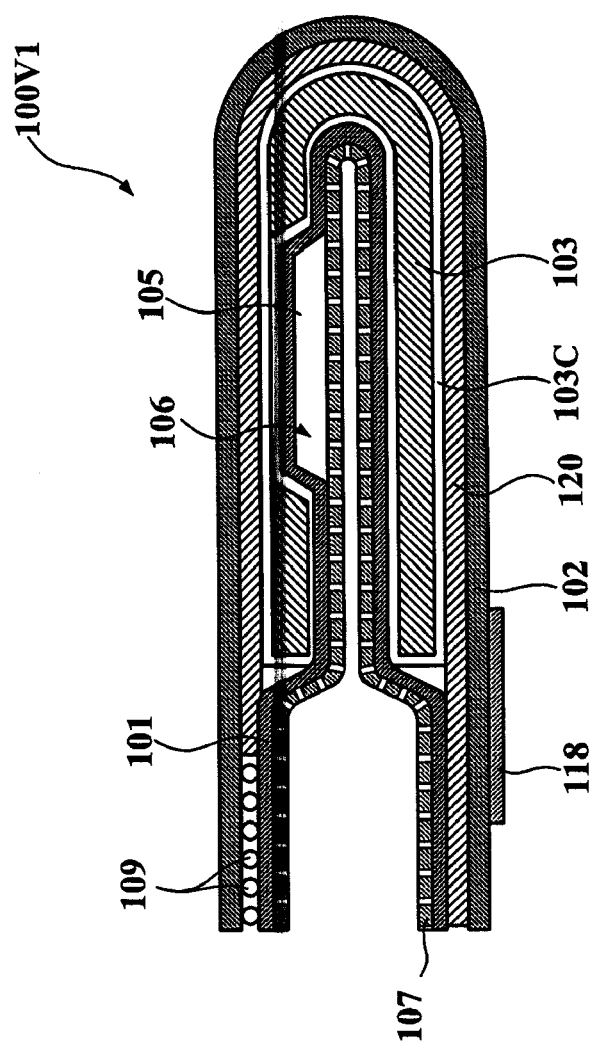
FIG. 17 is a cross sectional view in a product state of the tape type disposable diaper shown in FIG. 2.

FIG. 17 is a cross sectional view in a longitudinal direction of the tape type disposable diaper 100V1 in accordance with the first embodiment, and it shows a cross sectional structure in the product state of the present diaper 100V1.

As shown in FIG. 17, in the product state, if the present diaper 100V1 is folded into two in the longitudinal direction of the diaper body 104, so-called fold set does not reach the opening portion 106 of the feces pocket 105 even if the fold set is formed in the folded portion or the like, so that the wrinkle is not generated in the feces pocket 105. Accordingly, the feces pocket 105 is not changed in shape, whereby the excrement does not leak out in the outer peripheral direction of the feces pocket 105 as shown in an embodiment mentioned below, and the volumetric capacity of the feces pocket 105 does not become smaller. Further, since the aperture of the mesh sheet 107 in the portion covering the opening portion 106 of the feces pocket 105 does not break, the excrement does not stay on the front face of the present diaper 100V1. Accordingly, the excrement does not expand on the front face of the present diaper 100V1 and the hip of the wearer can always keep purity. Therefore, there can be obtained an advantage that the generation of the dermatitis or the skin irritation can be prevented, and cleaning up after is easier for a caregiver.

In this case, it is preferable that the tape type disposable diapers 100V2 to 100V5 in accordance with the other embodiments of the present invention are made in the aspect of folded into two in the longitudinal direction of the diaper body 104 in the product state, in the same manner as the present diaper 100V1.

Further, this folded aspect can be applied to known various absorbent articles. However, it is preferably applied particularly to the tape type disposable diaper because the above-mentioned advantages in the product state can be easily obtained.

EMBODIMENT

In order to confirm the effect of the folded aspect in the product state of the absorbent article in accordance with the present invention, there were prepared an absorbent article folded into two in the longitudinal direction, and an absorbent article folded into three in the longitudinal direction as mentioned below, and there was conducted consumer research on visual effects and hardness of leak of the feces of each of the absorbent articles. It should be noted that the present invention is not limited to these embodiments.

A result of the consumer research on the visual effects and the hardness of leak of the feces, with regard to each of the absorbent article folded into two in the longitudinal direction, and the absorbent article folded into three in the longitudinal direction, is as shown in Table 1. In this case, in the present embodiment, the tape type disposable diaper for baby was used as the absorbent article.

In this case, "visual effect" in Table 1 was obtained by a visual evaluation of a visual finish level of the absorbent articles, which was folded once and then expanded, viewed from the front face side, and the "visual effect" should leads to a stability of a quality achieving the hardness of leak of the feces mentioned below, that is, giving a sense of security visually.

Further, "hardness of leak of feces" is that the consumer conducted the amount at which the excrement leaks out in the outer peripheral direction of the feces pocket by the visual evaluation.

An evaluation standard is composed of five levels of "very satisfied" corresponding to 5 points, "satisfied" corresponding to 4 points, "neither satisfied nor dissatisfied" corresponding to 3 points, "dissatisfied" corresponding to 2 points, and "very dissatisfied" corresponding to 1 point.

TABLE 1

| monitor | visual effect | | hardness of leak of feces | |
| --- | --- | --- | --- | --- |
| | two-folded (point) | three-folded (point) | two-folded (point) | three-folded (point) |
| a | 4 | 4 | 5 | 4 |
| b | 5 | 4 | 4 | 3 |
| c | 4 | 3 | 5 | 3 |
| d | 5 | 3 | 5 | 4 |
| e | 4 | 4 | 4 | 4 |
| average | 4.4 | 3.6 | 4.6 | 3.6 |

From Table 1, with the two-folded in the product state of the absorbent article, the visual effect is good, and the excrement (particularly the feces) is hard to leak out of the feces pocket. Accordingly, it can be seen that the excrement does not expand on the front face of the absorbent article.

INDUSTRIAL APPLICABILITY

Figure 18:
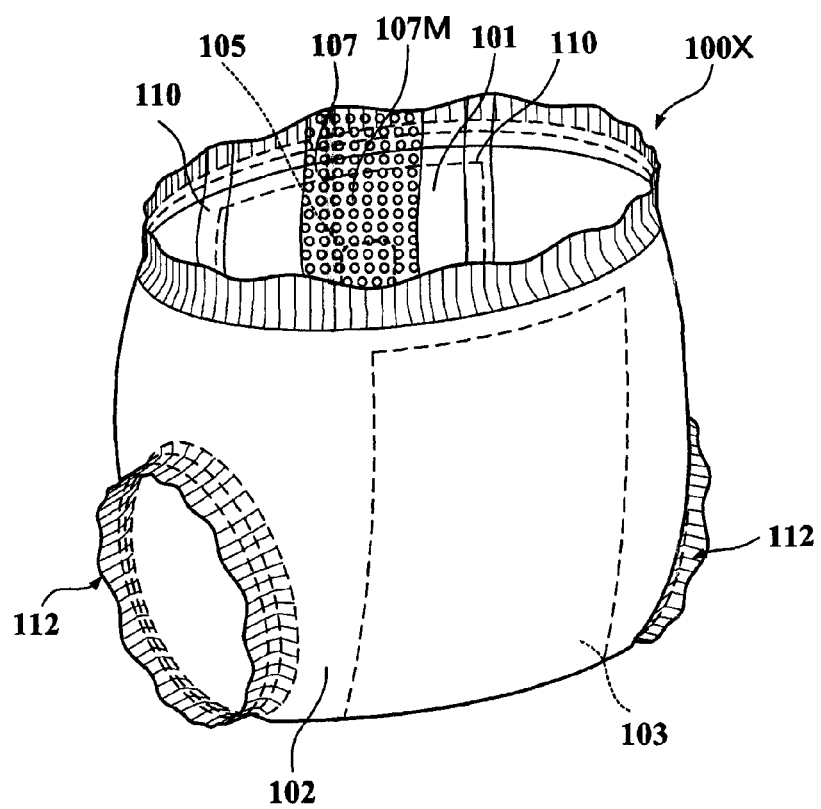
FIG. 18 is a perspective view of a pants type disposable diaper corresponding to a modified example of the present invention.
Figure 19:
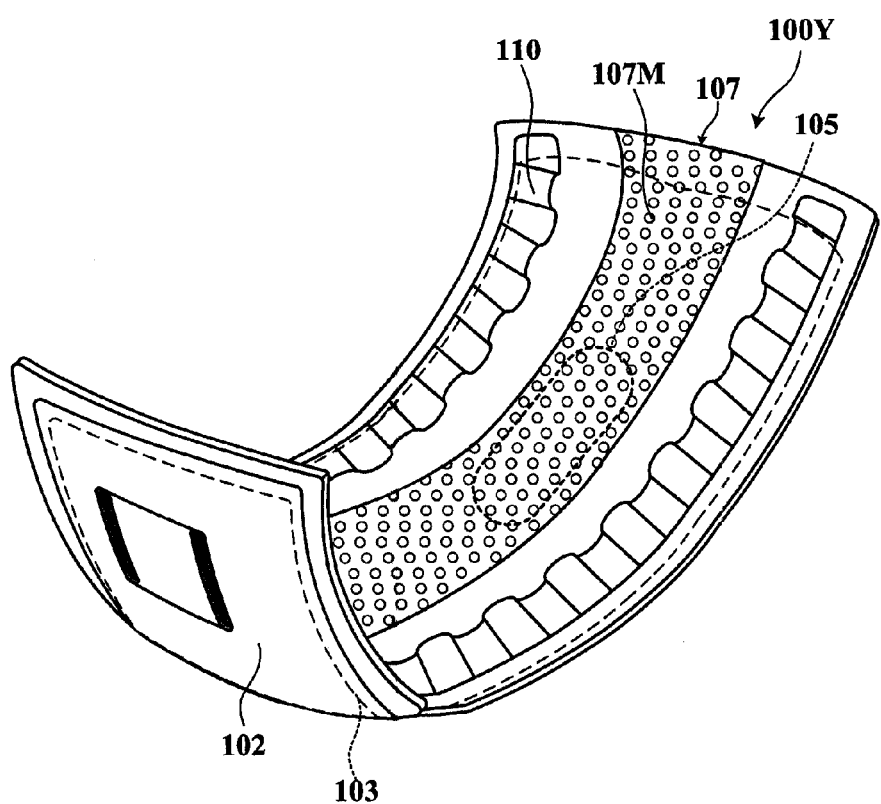
FIG. 19 is a perspective view of an incontinence pad corresponding to another modified example of the present invention.

The description is given above of the contents of the present invention in connection with the tape type disposable diaper for babies or adults, however, the present invention is not limited to the tape type disposable diaper, but may be applied to a pants type disposable diaper 100X as shown by a perspective view in FIG. 18, or an incontinence pad 100Y as shown in FIG. 19, and can be applied to the absorbent articles known in this field such as a training pants for babies or the like.

What is claimed is:

1. A disposable absorbent article structured such that an article body is composed of at least a top sheet arranged in a front face side, a back sheet arranged in a back face side, and an absorber interposed between the top sheet and the back sheet, and a feces pocket for storing and holding an excrement is provided in a hip contact portion of the article body, wherein the feces pocket is provided by forming a concave portion having a depth that only extends partway through the absorber in the thickness direction of the absorber, wherein the absorbent article is formed in a shape folded into two in a longitudinal direction of the article body in a product state, wherein an opening portion of the feces pocket is formed such that the opening portion of the feces pocket does not reach a folded portion formed by folding the absorbent article into two, wherein the opening portion of the feces pocket is covered with a mesh sheet and the top sheet, and wherein the excrement is stored and held between the mesh sheet and the top sheet in the feces pocket.

2. The absorbent article according to claim 1, wherein an open area ratio of the mesh sheet is between 15 and 30%.

3. The absorbent article according to claim 1, wherein a cross sectional shape of the opening portion of the feces pocket is formed in a broadened shape toward the front face side of the article body.

4. The absorbent article according to claim 1, wherein the absorbent article is a tape type disposable diaper having fastening tapes and a frontal tape, the fastening tapes have one end portion pasted to an end portion of a dorsal side region of the article body and a second end portion provided with a hook member, the frontal tape is pasted to an outer face of a ventral side region of the article body, and the fastening tapes are fastened to the frontal tape, and thereby the absorbent article is worn.

5. The absorbent article according to claim 1, wherein the top sheet has a hydrophilic nature, and the mesh sheet has a water repellant nature.

6. The absorbent article according to claim 1, wherein a plane shape of the feces pocket is formed in any one of a triangular shape expanding toward a dorsal side, a baseball home plate shape expanding toward a dorsal side, or heart shape expanding toward a dorsal side.

7. The absorbent article according to claim 5, wherein the mesh sheet having the water repellent nature is also coated with a hydrophilic agent, wherein a portion of the mesh sheet around the feces pocket is coated with more of the hydrophilic agent than a portion of the mesh sheet around a urine outlet portion of the absorbent article.

* * * * *